US009750672B1

(12) United States Patent
Wallach et al.

(10) Patent No.: US 9,750,672 B1
(45) Date of Patent: Sep. 5, 2017

(54) *ALOE* DERIVED MINERAL SUPPLEMENT

(71) Applicant: AL Global Inc., Chula Vista, CA (US)

(72) Inventors: Joel Wallach, Chula Vista, CA (US); Steve Wallach, Chula Vista, CA (US)

(73) Assignee: AL Global Inc., Chula Vista, CA (US)

( * ) Notice: Subject to any disclaimer, the term of this patent is extended or adjusted under 35 U.S.C. 154(b) by 0 days.

(21) Appl. No.: 14/166,306

(22) Filed: Jan. 28, 2014

Related U.S. Application Data

(60) Provisional application No. 61/757,520, filed on Jan. 28, 2013.

(51) Int. Cl.
| | | |
|---|---|---|
| *A61K 8/29* | (2006.01) | |
| *A23L 1/304* | (2006.01) | |
| *A61K 8/19* | (2006.01) | |
| *A61K 8/23* | (2006.01) | |
| *A61K 8/24* | (2006.01) | |
| *A61K 8/25* | (2006.01) | |
| *A61K 8/26* | (2006.01) | |
| *A61K 8/27* | (2006.01) | |
| *A61K 8/28* | (2006.01) | |
| *A61K 8/66* | (2006.01) | |
| *A61K 8/00* | (2006.01) | |
| *A61K 8/18* | (2006.01) | |
| *A61K 8/97* | (2017.01) | |
| *A61K 35/00* | (2006.01) | |
| *A61K 35/02* | (2015.01) | |

(52) U.S. Cl.
CPC ............... *A61K 8/29* (2013.01); *A23L 1/304* (2013.01); *A61K 8/19* (2013.01); *A61K 8/23* (2013.01); *A61K 8/24* (2013.01); *A61K 8/25* (2013.01); *A61K 8/26* (2013.01); *A61K 8/27* (2013.01); *A61K 8/28* (2013.01); *A61K 8/66* (2013.01)

(58) Field of Classification Search
None
See application file for complete search history.

(56) References Cited

U.S. PATENT DOCUMENTS

| | | | | |
|---|---|---|---|---|
| 5,925,357 | A | * | 7/1999 | Cerqueira et al. ............ 424/744 |
| 2004/0126460 | A1 | * | 7/2004 | Schrauzer ............... A23L 1/304 |
| | | | | 426/72 |
| 2010/0278940 | A1 | | 11/2010 | Neuls et al. |
| 2012/0322757 | A1 | * | 12/2012 | Coats et al. .................... 514/54 |

FOREIGN PATENT DOCUMENTS

| | | |
|---|---|---|
| WO | WO 9958575 A1 * | 11/1999 |
| WO | WO 2008140820 A2 * | 11/2008 |

OTHER PUBLICATIONS

Rajendran, V; et al; "Study on the Analysis of Trace Elements in Aloe Vera and its Biological Importance" Journal of Applied Sciences Research, 3, 1476-1478, 2007.*
Rajasekaran et al., "Mineral Contents of Aloe Vera Leaf Gel and Their Role on Streptozotocin-Induced Diabetic Rats", Biological Trace Element Research, vol. 108, pp. 185-195. (2005).
Schlussel, "Mineral Absorption and Deficiency", (approximately Apr. 2004).

* cited by examiner

*Primary Examiner* — David Berke-Schlessel
(74) *Attorney, Agent, or Firm* — Venable LLP; Keith G. Haddaway

(57) ABSTRACT

A composition containing minerals from *aloe* rind, and more particularly to compositions containing minerals derived from *aloe* rind by ashing or fermentation, and methods of preparing and using the compositions is disclosed. Formulations can includes *aloe* rind minerals and one or more additional active on inactive ingredients, and can be suitable for topical or oral administration. Method of maintaining or improving tissue health, for example, maintaining or improving bone health, maintaining or improving cardiovascular health, or improving the appearance or texture of skin by administering the *aloe* rind minerals are also disclosed.

12 Claims, No Drawings

ALOE DERIVED MINERAL SUPPLEMENT

FIELD OF THE INVENTION

The present invention relates generally to a composition containing minerals from *aloe* rind, and more particularly to compositions containing minerals derived from *aloe* rind by ashing or fermentation, and methods of preparing and using the compositions.

BACKGROUND

*Aloe* is a genus containing about 500 species of flowering succulent plants. The most common and well known being *Aloe Vera*, or "True *aloe*". The genus is native to Africa and is common in the Cape Province, the mountains of tropical Africa, the islands of Africa including Madagascar, and the Arabian Peninsula. It's been called "Plant of Immortality".

Most *aloe* species have a rosette of large, thick, fleshy leaves. The leaves are often lance-shaped with a sharp apex and a spiny margin. *Aloe* flowers are tubular, frequently yellow, orange, pink or red, and are present, often in dense clusters and hanging, at the apex of simple or branched, leafless stems. *Aloe* is used both topically and ingested. Most uses of *aloe* rely on its digestive soothing effects, saccharides (sugars) from the *aloe* gel, or whole leaf products. The inner gel of the *aloe* leaf contains the inner leaf juice and is commonly used for the gel which has a soothing effect on the skin and is used topically in skin care products such as sun care products for sun burn, and can also be consumed. The *aloe* latex is a sappy material between the inner gel and the outer leaf. The inner gel and latex are sometimes referred to as the *aloe* fillet. The outer layer of the *aloe* leaf is the rind, which is generally considered waste. Other common uses of *aloe* include laxative, weight management, digestive aid, skin care, enzyme and saccharide source.

Sources of calcium and magnesium are of high interest as calcium and magnesium are commonly used in the human and animal health and wellness industry for supplements, skin care and pharmaceutical products. Calcium is essential for living organisms, in particular in cell physiology, where movement of the calcium ion into and out of cytoplasm functions as a signal for many cellular processes. As a major material used in mineralization of bone, teeth and shells, calcium is the most abundant metal by mass in many animals.

Common sources of dietary calcium are from foods such as dairy, green leafy vegetables, meat and poultry as well as dietary supplements. Calcium supplements are among the top consumed dietary supplements. Calcium and magnesium in dietary supplements typically comes from inorganic sources such as oyster shell, coral, mined sources including ancient sea bed sources (diatomaceous earth), and limestone.

There are no commonly available plant sources for calcium or magnesium supplements. Calcium sourced from a living plant would be expected to have a higher bioavailability than non-plant sources. This could arise, in part, from the association of the polysaccharides associated with the plant source.

BRIEF SUMMARY

The present invention is a composition that includes minerals prepared from *aloe* leaf rind. The *aloe* leaf rind used to prepare the composition can be free from other parts of the *aloe* leaf. In exemplary embodiments, the composition is prepared by burning, fermenting or extracting the *aloe* rind. The compositions of the invention include calcium and magnesium, for example in a ratio of about 3:1. The composition can further include phosphorous potassium and strontium. The composition can be substantially free of lead, cadmium and mercury. In some embodiments, the composition can include less than 200 ppm of aluminum and/or less than 10 ppm nickel. Compositions, particularly those obtained by fermentation can include one or more of enzymes, amino acids, or other phyto-nutrients.

In other embodiments, the invention is a formulation that includes *aloe* rind minerals of the invention and one or more additional active on inactive ingredients. The formulation can be, for example a dietary supplement that includes *aloe* rind minerals of the invention. Dietary supplements can also include other vitamins, minerals, amino acids, anti-oxidants, other bone building ingredients, or enzymes not from *aloe* rind. The dietary supplement can be in the form of a powder, tablet or capsule. Formulations according to the invention can also be a topical composition. For example, the formulation can be in a form suitable for topical administration such as a lotion, cream, ointment, salve or other emulsion.

Aspects of the invention also include a method of making a mineral composition from *aloe* leaf rind. An exemplary method includes the steps of separating *aloe* leaf rind from the *aloe* gel and inner leaf and burning the separated *aloe* leaf rind to produce an ash. The method can also include drying the *aloe* leaf rind before burning. Another method of preparing a composition of the invention includes the steps of separating *aloe* leaf rind from the *aloe* gel and inner leaf and optionally drying the *aloe* leaf rind; fermenting the separated *aloe* leaf rind to provide a fermented rind; concentrating the fermented rind; and optionally drying the concentrated fermented rind.

In an aspect, the invention is also a method of maintaining or improving tissue health. For example, the method can include maintaining or improving bone health, maintaining or improving cardiovascular health, or improving the appearance or texture of skin by administering a composition that includes *aloe* rind minerals according to the invention. The composition can be administered, for example, orally or topically. Further objectives and advantages, as well as the structure and function of preferred embodiments will become apparent from a consideration of the description, drawings, and examples.

DETAILED DESCRIPTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Although *aloe* is commonly used as a source for medicaments, the outer leaf or rind is usually considered to be waste or a by-product and is typically disposed of or used as compost. Although there are some "whole leaf" *aloe* products, *aloe* rind is not commonly used in *aloe* based products and its presence in the whole leaf product is commonly a matter of convenience for processing rather than for any benefit that the rind could provide. After detailed testing using ICP/mass spectrometry it has been discovered that

*aloe* rind contains a rich source of calcium and. *Aloe* rind also contains other trace minerals that can act as co-factors and aid with the body's absorption and utilization of these minerals. These additional trace minerals include, for example, phosphorus, potassium, and strontium. The present invention is directed to a composition derived from *aloe* rind for use as a dietary supplement of topical composition. The invention is also a method for preparing the inventive compositions.

The use of mineral derived from plants provides several advantages over minerals obtained from other materials. For example, the ability to document the history of a living plant source allows for a better knowledge base of what the plant may contain. For example, the location, growth conditions, e.g. certification of organically farmed, type of soil, etc. can be recorded and known to individuals manufacturing or consuming the minerals. Plant sources also provide a renewable resource of minerals rather than a destructive extraction from the earth. Plants can be a rich source of calcium and magnesium, along with other co-factors that are beneficial to heath in general and particularly bone health (bone building, maintenance of bone density, etc.), joint health and cardiovascular health. Because *aloe* rind has been found to be a high calcium/magnesium content source, it is an especially valuable source to provide any health benefit related to calcium and magnesium. In some embodiments, because *aloe* rind is a plant source, it can also add benefits by increasing bioavailability of magnesium and calcium because the minerals, as well as co-factors, enzymes, amino acids and other phyto-nutrients, are from a living plant source that provides a balanced mixture of minerals. Such benefits be can derived from the naturally occurring mixture or ratio of minerals that are present or by the presence of additional enzymes, amino acids and other phyto-nutrients that are beneficial to health. Use of a living plant as a mineral source provides many advantages. *Aloe* is well known and recognized for its medicinal properties, providing and identifiable source and can be from a verified and certified organic source creating further appeal over the other common sources of calcium, magnesium and other materials that are currently available. Thus, *aloe* rind as a potential dietary supplement ingredient has other advantages.

The present invention is related to mineral supplements obtained from *aloe* rind. The minerals can be isolated in a number of ways including, by way of example and not limitation, burning or ashing, fermentation and extraction. As a preliminary step in most preparations, the outer *aloe* leaf or rind is removed and separated from the inner fillet of the *aloe* leaves and the rind is cleaned. In most instances, the rind is dried until most of the moisture content is eliminated. As discussed above, rather than being a discarded waste product with no assumed nutritive value, the use of the rind in the present invention is novel and not an obvious variation of current practices in the art.

In *aloe* rind materials treated according to the present invention, calcium and magnesium can make up about 50-75% of the mineral content. About 40-60%, and typically about 45-50%, of the total mineral content is calcium. Magnesium makes up approximately 10-20%, typically about 12-17%, of the total mineral content. While calcium can often be obtained through dietary sources, magnesium levels are frequently inadequate in the diet. *Aloe* rind minerals of the invention contain a ratio of calcium:magnesium that can vary from about 1.5:1 to about 5:1. In typical preparations, the calcium:magnesium ratio is about 3:1. The Recommended Dietary Allowance (RDA) of calcium and magnesium varies due to age and health status, however the range of calcium and magnesium ratio is from 2:1 to 4:1 (Calcium to Magnesium). For active teens and elderly adults, the 3:1 (Calcium to Magnesium) fits with the RDA nearly perfectly. As this is a "supplement" and not meant to replace all sources of Calcium and Magnesium the 3:1 is beneficial for all age groups.

The human body requires new supplies of nutrients and adequate and appropriate reserves of nutrients for proper metabolic and structural function. There is evidence that nutritional need for mineral intakes are not being met. Although supplementation with minerals is recommended to prevent deficiencies, there is growing evidence suggesting that minerals contained in many commonly available supplements are not always readily absorbed and taken up by the consumer. Mineral absorption is complicated and dependent upon a number of factors related to mineral solubility and absorbability. Absorption is the rate at which and the process by which molecules and atoms from the environment enter the interior of the organism via passage across (or around) the lining cells of the gastro-intestinal tract. Absorption can occur all the way from the stomach to the rectum, although the small intestine is the organ most importantly involved in absorption. Current knowledge on intestinal absorption of nutrients and minerals includes multiple factors that can affect their absorption including their solubility and bioavailability.

Indeed, it is known in the art that by increasing the solubility of a mineral, one can increase its bioavailability and improve its absorption. For example, when magnesium oxide and magnesium citrate are compared with respect to their in vitro solubility and in vivo gastrointestinal absorbability, the more soluble salt was observed to have increased absorption. (Lindberg J S, Zobitz M M, Poindexter J R, Pak C Y. Magnesium bioavailability from magnesium citrate and magnesium oxide. *J Am Coll Nutr* 1990 February; 9(1):48-55.) Magnesium oxide was virtually insoluble in water and only 43% soluble in simulated peak acid secretion (24.2 mEq hydrochloric acid/300 ml). Magnesium citrate had high solubility even in water (55%) and was substantially more soluble than magnesium oxide in all states of acid secretion. The increment in urinary magnesium following magnesium citrate load (25 mmol) was significantly higher than that obtained from magnesium oxide load (during 4 hours post-load, 0.22 vs 0.006 mg/mg creatinine, p<0.05; during second 2 hours post-load, 0.035 vs 0.008 mg/mg creatinine, p less than 0.05). Thus, magnesium citrate was more soluble and bioavailable than magnesium oxide. Similarly, it is known in the art that preparing salt forms with improved water solubility enhances the bioavailability of calcium.

The use of plant derived *aloe* rind minerals also provides advantages for bioavailability. It is well known that calcium and magnesium are typically not well absorbed, but are better absorbed from plant and food sources. As discussed above, mineral absorption is complicated and dependent upon a number of factors related to mineral solubility and bioavailability. The *aloe* plant has already processed and accumulated beneficial minerals through the photosynthesis process. The relative amounts or ratios of these beneficial minerals, including and in addition to calcium and magnesium, are the same as expected to be obtained in other plant sources that are known to have improved bioavailability. Accordingly, the use of plant derived mineral material in general, and *aloe* derived minerals in particular is better suited for promoting absorption if calcium and magnesium. The invention also provides magnesium, calcium and other minerals in a highly soluble form. The water solubility of the mineral material of the invention is 15% or higher and can be 17% or higher or about 20%. Moreover, the solubility of the *aloe* rind minerals of the invention is even higher in an acidic environment such as in stomach acid. The solubility in simulated stomach acid can be 75% or greater, 80% or higher, 85% or higher or about 88-90%. In one experiment, minerals obtained from *Aloe* rind using this invention were found to be 88.2% soluble in solution that simulates mammalian stomach acid (4% acetic acid solution). Thus, these minerals are more bioavailable than traditional Calcium and Magnesium sources such as oyster shell, mined calcium or magnesium from ancient sea bed materials or lime stone.

*Aloe* rind mineral of the invention provide a unique source of calcium and magnesium and contains an ideal mineral composition for use as a bone, joint and cardiovascular health supplement ingredient.

*Aloe* rind mineral according to the invention can include the minerals shown in Table 1.

TABLE 1

Mineral Content of Aloe Rind Minerals of the Invention

| Mineral | Content* (Range, %) | Content* (Typical, %) |
| --- | --- | --- |
| Aluminum | 0-0.05 | 0.0310 |
| Arsenic | 0-0.00015 | 0.0001 |
| Barium | 0-0.025 | 0.0175 |
| Boron | 0-0.03 | 0.0200 |
| Calcium | 40-60 | 48.7749 |
| Chromium | 0-0.0005 | 0.0003 |
| Copper | 0.001-0.003 | 0.0022 |
| Iron | 0.01-0.05 | 0.0377 |
| Lithium | 0.001-0.0075 | 0.0049 |
| Magnesium | 10-20 | 15.0759 |
| Manganese | 0.0005-0.005 | 0.0020 |
| Molybdenum | 0-0.0005 | 0.0003 |
| Nickel | 0-0.0005 | 0.0003 |
| Phosphorus | 2-5 | 3.3256 |
| Potassium | 10-20 | 16.6278 |
| Rubidium | 0-0.01 | 0.0098 |
| Sodium | 10-20 | 15.5193 |
| Strontium | 10-20 | 0.4877 |
| Titanium | 0.01-0.10 | 0.0488 |
| Zinc | 0.005-0.025 | 0.0140 |

*Content as indicated is the amount of each mineral as a percentage of the total mineral content as shown in Table 2.

In addition to calcium and magnesium, *aloe* rind minerals according to the invention can include other beneficial minerals such as phosphorous, potassium and strontium. In embodiments, phosphorous can make up about 2-5% of the total mineral content. In embodiments, potassium can make up about 10-20% of the total mineral content. In embodiments, strontium can make up about 10-20% of the total mineral content. The presence of copper, manganese, boron, and particularly strontium, even in trace amounts, provides further benefits. These minerals aid in absorption and utilization of other major mineral components, including calcium and magnesium. Phosphorus and potassium are also major minerals found in the *aloe* rind and are known essential minerals; both are also beneficial to muscle and bone health.

*Aloe* rind mineral according to the invention is substantially free of lead, cadmium, mercury, arsenic and uranium. The total mineral content of *aloe* rind mineral according to the invention can include contain less than about 0.03% aluminum and less than about 0.0003% nickel. Typical forms of calcium found in supplements contain measurable lead levels. Calcium and lead tend to be present together in mineral deposits in much the same way as for gold and quartz. Typical mined or sea sourced calcium supplements often have lead associated with them. Lead is of course an undesirable metal that can be found in calcium supplements to the point where lead content is closely monitored by the state of California, for measurable lead levels and a Proposition 65 Hazard Warning is mandatory. Since the *Aloe* Rind Mineral show no detectable lead, this is another significant advantage of this natural source.

California's Safe Drinking Water Enforcement Act of 1986, better known as Proposition 65 ("Prop 65"), requires that a company must warn consumers if marketing a product that contains a chemical that the State has determined may cause cancer, birth defects and/or reproductive harm. There are over 800 chemicals and substances on the Prop 65 List (See oehha.ca.gov). Prop 65 also allows private persons or organizations to bring actions against alleged violators on behalf of the "general public." The potential costs are high—failure to comply with Prop 65 can lead to fines of up to $2,500 per day, per violation, and plaintiffs are entitled to reimbursement of attorneys' fees. Prop 65 lawsuits can also be severely detrimental to a company's overall brand and public image. According to Prop 65, the amounts of lead, cadmium, arsenic and mercury are limited to the following:

| Mineral | NSRL or MADL (µg/clay)* |
| --- | --- |
| Arsenic | 10 |
| Cadmium | 4.1 |
| Lead | 15 |
| Mercury | None |

*NSRL = No Significant Risk Level
MADL = Maximum Allowable Daily Limit

*Aloe* rind mineral of the present invention are substantially free of one or more of lead, cadmium, arsenic and mercury. Substantially free of lead means that the composition contains an amount of lead that provides less than 15 µg/day when administered at the suggested dosage. For example, if the suggested dosage is 100 mg per day, the composition contains less than 1.5 µg lead. In exemplary embodiments, substantially free of lead means the composition contains lead in an amount of contains 15 ppm or less; in an amount of contains 10 ppm or less; in an amount of contains 5 ppm or less; in an amount of contains 2 ppm or less; in an amount of contains 1 ppm or less; or in an amount of contains 0.5 ppm or less. In exemplary embodiments, the composition contains no detectable lead.

Substantially free of arsenic means that the composition contains an amount of arsenic that provides less than 15 µg/day when administered at the suggested dosage. For example, if the suggested dosage is 100 mg per day, the composition contains less than 1.0 µg arsenic. In exemplary embodiments, substantially free of arsenic means the composition contains arsenic in an amount of contains 10 ppm or less; in an amount of 5 ppm or less; in an amount of 2 ppm or less; in an amount of 1 ppm or less; or in an amount of 0.5 ppm or less. In exemplary embodiments, the composition contains no detectable arsenic.

Substantially free of cadmium means that the composition contains an amount of cadmium that provides less than 4.1 µg/day when administered at the suggested dosage. For example, if the suggested dosage is 100 mg per day, the composition contains less than 0.41 µg cadmium. In exemplary embodiments, substantially free of cadmium means the composition contains cadmium in an amount of contains 10 ppm or less; in an amount of 5 ppm or less; in an amount of 2 ppm or less; in an amount of 1 ppm or less; in an amount of 0.5 ppm or less; or in an amount of 0.1 ppm or less. In exemplary embodiments, the composition contains no detectable cadmium.

Substantially free of mercury means that the composition contains an amount of mercury that provides less than 5 μg/day when administered at the suggested dosage. For example, if the suggested dosage is 100 mg per day, the composition contains less than 0.5 μg mercury. In exemplary embodiments, substantially free of mercury means the composition contains mercury in an amount of contains 10 ppm or less; in an amount of 5 ppm or less; in an amount of 2 ppm or less; in an amount of 1 ppm or less; or in an amount of 0.5 ppm or less. In exemplary embodiments, the composition contains no detectable mercury.

In one embodiment of a process of making *aloe* rind minerals according to the invention, *aloe* rind minerals are obtained by burning of the *aloe* rind to form an ash. When the *aloe* rind minerals are isolated by an ashing process, the cleaned and dried rind is burned leaving ash behind. A typical sample of the ash contains the minerals shown in Table 2.

TABLE 2

Mineral Content of aloe Rind Ash

| Mineral | Content (ppm) | Reporting Limit | Mineral | Content (ppm) | Reporting Limit |
|---|---|---|---|---|---|
| Aluminum | 140 | | Neodymium | ND | 0.5 |
| Antimony | ND | 0.5 | Nickel | 1.2 | |
| Arsenic | 0.58 | | Niobium | ND | 0.5 |
| Barium | 79 | | Osmium | ND | 0.5 |
| Beryllium | ND | 0.5 | Palladium | ND | 0.5 |
| Bismuth | ND | 0.5 | Phosphorus | 15,000 | |
| Boron | 90 | | Platinum | ND | 0.5 |
| Cadmium | ND | 0.5 | Potassium | 75,000 | |
| Calcium | 220,000 | | Praseodymiu | ND | 0.5 |
| Cerium | ND | 0.5 | Rhenium | ND | 0.5 |
| Cesium | ND | 0.5 | Rhodium | ND | 0.5 |
| Chromium | 1.5 | | Rubidium | 44 | |
| Cobalt | ND | 0.5 | Ruthenium | ND | 0.5 |
| Copper | 9.9 | | Samarium | ND | 0.5 |
| Dysprosium | ND | 0.5 | Scandium | ND | 0.5 |
| Erbium | ND | 0.5 | Selenium | ND | 1.0 |
| Europium | ND | 0.5 | Silver | ND | 0.5 |
| Gadolinium | ND | 0.5 | Sodium | 70,000 | |
| Gallium | ND | 0.5 | Strontium | 2,200 | |
| Germanium | ND | 0.5 | Tantalum | ND | 0.5 |
| Gold | ND | 0.5 | Technetium | ND | 0.5 |
| Hafnium | ND | 0.5 | Terbium | ND | 0.5 |
| Holmium | ND | 0.5 | Thallium | ND | 0.5 |
| Indium | ND | 0.5 | Thorium | ND | 0.5 |
| Iridium | ND | 0.5 | Thulium | ND | 0.5 |
| Iron | 170 | | Tin | ND | 5 |
| Lanthanum | ND | 0.5 | Titanium | 220 | |
| Lead | ND | 0.5 | Tungsten | ND | 0.5 |
| Lithium | 22 | | Uranium | ND | 0.5 |
| Lutetium | ND | 0.5 | Vanadium | ND | 1.0 |
| Magnesium | 68,000 | | Ytterbium | ND | 0.5 |
| Manganese | 9.1 | | Yttrium | ND | 0.5 |
| Mercury | ND | 0.5 | Zinc | 63 | |
| Molybdenum | 1.4 | | Zirconium | ND | 0.5 |

As can be seen from these results, the amount of calcium and magnesium is high as about 30% of the overall material and about 65% of the mineral content. Calcium makes up approximately 22% of the ash material and about 50% of the mineral content. Magnesium makes up approximately 7% of the ash material and about 15% of the mineral content. The *aloe* rind thus contains a unique 3:1 ratio of calcium: magnesium. As would be known to persons in the art, the minerals above are most commonly in the ionic (typically cationic) form and paired with counterions (typically anions) that are also derived from the plant. Counterions can include, for example, carbonates, sulfates, phosphates, halides (chlorides iodides, bromides) or others. Some minerals may be present as part of the counterions to other minerals. For example, boron may be present as borate. It is clear from these data that *aloe* rind minerals obtained from *aloe* rinds per the methods disclosed and suggested herein provide a unique source of calcium and magnesium and contain an ideal mineral composition for use as a bone, joint and cardiovascular health supplement ingredient.

Importantly, undesirable minerals such as aluminum, lead, cadmium, arsenic, mercury, nickel, etc. are absent or present at relatively low levels. Lead, which is commonly present in measurable amounts in many earth and sea derived calcium sources, is absent from the *aloe* rind minerals.

It also important to note that the invention provides a mineral composition that is distinct from alternative *aloe* leaf-derived products common in the art. As such, the mineral composition obtained by practicing the invention provides unique ratios of minerals that are advantageous for the purposes disclosed herein and largely excludes the presence of undesirable and potentially toxic minerals such as lead, cadmium, mercury, arsenic and uranium. Ashed *Aloe Vera* leaf gel compositions common in the art typically contain much greater concentrations of iron and lead, among other elements (Table 3 and Rajasekaran et al., 2005), than the invention. As such, the ratios of iron:calcium and iron: magnesium are about 25:1 and 22:1, respectively. In contrast, the invention provides for 1,294 times more calcium than iron, and 400 times more magnesium than iron (from Table 2). In addition, the invention does not contain detectable levels of the potentially toxic compound, lead (Table 2), whereas common ashed *Aloe Vera* leaf gel compositions contain nearly a 1:1 ratio of calcium to lead. This last fact is an unexpected finding as it is uncommon to see a composition of minerals derived from a single source contain such a large concentration of calcium without an accompanying large concentration of lead. For example, California recognizes that lead naturally occurs within calcium at the rate of 0.8 ppm (or 0.8 micrograms/gram).

TABLE 3

Trace Elements Present in Aloe Vera Leaf Gel Ash (from Rajasekaran et al., 2005)

| Elements | Concentration of elements (mg/2g) |
|---|---|
| Iron | 3.5 |
| Copper | 0.15 |
| Calcium | 0.141 |
| Zinc | 0.378 |
| Manganese | 0.631 |
| Lead | 0.138 |
| Chromium | 0.146 |
| Vanadium | 0.32 |
| Potassium | 0.397 |
| Sodium | 0.162 |
| Magnesium | 0.157 |

Another way to produce *aloe* rind minerals according to the invention is through fermentation. Fermentation is commonly used in food production and in producing some dietary supplements. It is often used to produce phytonutrient and enzyme ingredients and some anti-oxidants or is associated with macro biotic products. Phyto-nutrients present in *aloe* rind can include, for example, acetylated mannans, polymannans, anthraquinone, C-Glycosides, anthrones, anthraquinones, such as emodin, lectins, simple and complex saccharides, polysaccharides and others. Fermented *aloe* rind can also include other beneficial nutrients such as vitamins, enzymes, proteins, peptides, fatty acids and the like.

Fermentation is a longer process, but avoids the use of high heat to provide the *aloe* rind minerals of the invention. This preserves or avoids complete degradation of other biologically active plant components, such as amino acids or enzymes, that could also help the body to assimilate the *aloe* rind minerals at a higher rate or level. Beneficial nutrients such as enzymes, amino acids, or phyto-nutrient compounds are likely destroyed when burning the leaves. Fermentation uses bacteria and or yeast to breakdown the rind material and reduce the organic material. In the present invention, the *aloe* leaf rind is reduced to its mineral content. However, in some embodiments the fermented product also includes other plant compounds including, for example, nutrients such as enzymes, amino acids, or phyto-nutrient compounds.

Fermentation involves the same steps of accumulating the outer *aloe* leaf, however also would include the biological breakdown of the leaves. The liquid would then be concentrated. The composition can be provided as the concentrated fermentation product. The concentrated fermentation product is dried to arrive at a finished solid *aloe* rind mineral material. The fermented material includes a similar mineral composition as the ash, although there are obviously additional components so that the overall mineral content is lower. However, the fermented material also can include enzymes, amino acids, or other phyto-nutrients as described above.

The *aloe* rind mineral according to the invention can utilized in a number of ways. Generally, the *aloe* rind mineral of the invention is used as a dietary supplement to provide a source of calcium, magnesium and other minerals to promote health in general and bone, joint and cardiovascular health in particular. In some embodiments, the *aloe* rind mineral of the invention is used in dry form without mixing. The *aloe* rind minerals can then be utilized as a powder for consumption such as by mixing with other foods or food ingredients, or by administration in a capsule. In other embodiments, the *aloe* rind mineral of the invention is mixed with other suitable diluents or excipients to form a powder for consumption or that can be placed into a capsule, or manufactured into a tablet. The *aloe* rind mineral of the invention can be used alone or can be added to other formulations to provide dietary supplement formulas and formulations that include other beneficial ingredients. Other beneficial ingredients can include, but are not limited to, vitamins, minerals, amino acids, anti-oxidants, other bone building ingredients, enzymes, etc. Vitamin D3 is a particularly beneficial additive in that it can further improve calcium and magnesium absorption as well as phosphorous absorption. Supplements can be administered to any organism that would benefit from the minerals including reptiles, amphibians, and mammals. Thus the inventive material can be used as an ingredient for animal supplements and animal feed products. Exemplary supplements are particularly beneficial to humans.

*Aloe* rind materials of the present invention provide additional advantages over other mineral supplements, particularly calcium supplements. For example, many Calcium sources are bitter, making it difficult to create a palatable flavor profile. *Aloe* find mineral compositions of the present invention are milder and have a more favorable taste profile allowing for a broader range of product creation opportunities as compared to other sources of minerals, Calcium and Magnesium in particular. Additionally, whereas most Calcium sources are gritty and require extensive grinding (milling) when used in creams, liquids or lozenges, *aloe* rind minerals of the present invention are less gritty or grainy, vastly minimizing the need to mill the material saving on production time and wear and tear on expensive machines, as well as providing a more palatable and comfortable material for oral and topical uses. Finally, the *aloe* rind minerals of the invention tend to be alkaline with a relatively high pH. Alkaline products are generally desirable and have a high value in the marketplace.

In other embodiments the material is used as an additive to other products where the minerals and/or other plant derived compounds can be beneficial. For example, the material can be incorporated into creams, lotions and emulsions for topical administration. According to these embodiments, the material is incorporated into skin and hair care products.

The *aloe* rind mineral of the invention can be used to provide a wide range of benefits. The *aloe* rind mineral of the invention is useful in promoting and maintaining bone health. For example, *aloe* rind minerals according to the invention can be used in methods and materials for promoting and maintaining bone density and growth. *Aloe* rind mineral of the invention are also useful in promoting and maintaining joint health and cardiovascular health. Typical dosages for *aloe* rind minerals can be based on the amount of calcium or magnesium as the remaining minerals are present in beneficial amounts based on the amount of calcium or magnesium. Exemplary embodiments include dosages adequate to provide a calcium daily dosage (delivered at once or in 2-5 equally divided doses through the day) of for example, 100-2000 mg of calcium, for example 250-1000 mg, 250-500 mg or 500-1000 mg. Exemplary compositions include calcium in an amount of 100 mg per dose, 200 mg per dose, 250 mg per dose, 300 mg per dose, 350 mg per dose, 400 mg per dose, 450 mg per dose, 500 mg per dose, 600 mg per dose, 700 mg per dose, 800 mg per dose, 900 mg per dose, or 1000 mg per dose. Exemplary embodiments include dosages adequate to provide a magnesium daily dosage (delivered at once or in 2-5 equally divided doses through the day) of for example, 40-1500 mg of calcium, for example 50-500 mg, 100-200 mg or 200-500 mg. Exemplary compositions include 40 mg per dose, 50 mg per dose, 75 mg per dose, 100 mg per dose, 130 mg per dose, 150 mg per dose, 200 mg per dose, 250 mg per dose, 300 mg per dose, 350 mg per dose, 400 mg per dose, 450 mg per dose, or 500 mg per dose.

Embodiments of the invention include methods of maintaining health by administering *aloe* rind mineral according to the invention. In one embodiment, the invention is a method of maintaining bone health by administering *aloe* rind mineral according to the invention. Another embodiment of the invention is a method of maintaining joint health by administering *aloe* rind mineral according to the invention. Yet another embodiment of the invention is a method of maintaining cardiovascular health by administering *aloe* rind mineral according to the invention.

In exemplary embodiments of methods according to the invention, the amount administered is an effective amount to achieve the desired effect or benefit. The effective amount will vary among individuals. For example, in a relatively healthy individuals seeking to maintain bone health, an effective amount is the amount necessary to provide a recommended daily allowance of one or more minerals within the *aloe* rind mineral of the invention. For a person in need of improvement of bone health, an effective amount would be the amount of *aloe* rind mineral according to the invention needed to be consumed to produce a desired biological level, for example a particular plasma concentration, of one or more minerals in the *aloe* rind minerals of the invention. The particular doses of the *aloe* rind mineral of the invention would be known to persons skilled in the art.

EXAMPLES

Example 1—Preparation of Composition

In a typical method of preparing *aloe* rind minerals, the *aloe* plant is cultivated for approximately 24 months before harvesting. In exemplary embodiments, cultivation is documented in a manner that provides for Certified Organic status. After harvesting, the leaves are removed by cutting at the base, and the outer leaf is removed by filleting the individual leaf The gel is removed from the center of the individual leaf, leaving two outer Leaf pieces. The outer leaf or rind is then isolated from the gel which is then processed separately and for different uses. The outer leaf is then cleaned, inspected and sent for drying or for the fermentation.

Drying can be done by air drying or heat drying, the purpose is to remove the moisture content, leaving the dried outer leaf. The dried leaves are then turned to ash by combustion. No additives or accelerants are used, the *aloe* simply is burned much like dry tree leaves would burn. The ash is put through a strainer process using stainless steel screens. This ensures only ash proceeds to the next step. The ash is inspected, tested for assay, and packed for use. Uses can include supplements, skin care, pet products, etc.

Example 2—Mineral Analysis

A sample of *aloe* rind was ashed at 700° C. The ash was then microwave digested with nitric acid, transferred to a plastic bottle and diluted with deionized water. Semiquantitative analysis was carried out using Inductively Coupled Plasma-Mass Spectrometry (ICP-MS) and Inductively Coupled Optical Emission Spectroscopy (ICP-OES).

The ICP-MS multi-element scan includes most metals and some nonmetals. It omits some elements (for example, C, Cl, N, O, F and H) which may be present in samples. Other instrumental techniques were used to supplement the analytical results produced by ICP-MS. Analyses for selected elements were carried out quantitatively by ICP-OES.

Solubility testing was carried out with two methods: dissolution in water and also a 4% acetic acid solution.

The Loss On Ignition (LOI) at 700° C. was 6.39%. The test results are shown below. The listed mineral elements were the only elements detected at the detection limits attainable on this sample matrix using the techniques available. The concentrations of all the elements determined above the limit of detection in the sample are given in units of micrograms per gram (parts per million). These results are semiquantitative. The reported concentrations apply to the original sample before it was ashed.

| Element | Concentration ppm | Element | Concentration ppm |
|---|---|---|---|
| aluminum | 300 | molybdenum | 1.8 |
| antimony | 0.22 | neodymium | 0.60 |
| barium | 760 | nickel | 6.0 |
| bismuth | 1 | niobium | 0.028 |
| boron | 270 | phosphorus | 19,000 |
| calcium | 250000 | potassium | 38,000 |
| cerium | 1.1 | praseodymium | 0.19 |
| cesium | 0.26 | rhenium | 0.021 |
| chromium | 1.3 | rubidium | 34 |
| cobalt | 0.55 | samarium | 0.090 |
| copper | 26 | silicon | 230 |
| dysprosium | 0.054 | sodium | 56,000 |
| erbium | 0.030 | strontium | 1,600 |
| europium | 0.16 | sulfur | 15,000 |
| gadolinium | 0.12 | tantalum | 0.002 |
| gallium | 0.19 | terbium | 0.013 |
| hafnium | 0.013 | thorium | 0.15 |
| holmium | 0.011 | thulium | 0.005 |
| iron | 420 | tin | 0.09 |
| lanthanum | 1.4 | titanium | 21 |
| lithium | 5.8 | uranium | 0.020 |
| lutetium | 0.003 | vanadium | 0.62 |
| magnesium | 54,000 | ytterbium | 0.023 |
| manganese | 390 | yttrium | 0.60 |
| zinc | 94 | | |
| zirconium | 0.37 | | |

The detection limits of the method employed are as follows:

| Element | Detection Limit (ppm) | Element | Detection Limit (ppm) | Element | Detection Limit (ppm) |
|---|---|---|---|---|---|
| aluminum | 5 | indium | 0.05 | ruthenium | 0.05 |
| antimony | 0.1 | iodine | 0.5 | samarium | 0.002 |
| arsenic | 0.5 | iridium | 0.005 | scandium | 1 |
| barium | 0.1 | iron | 5 | selenium | 10 |
| beryllium | 0.05 | lanthanum | 0.01 | silicon | 100 |
| bismuth | 1 | lead | 0.5 | silver | 0.1 |
| boron | 10 | lithium | 1 | sodium | 10 |
| bromine | 100 | lutetium | 0.002 | strontium | 1 |
| cadmium | 0.1 | magnesium | 1 | sulfur | 100 |
| calcium | 1 | manganese | 1 | tantalum | 0.002 |
| cerium | 0.1 | mercury | 0.5 | tellurium | 0.1 |
| cesium | 0.1 | molybdenum | 0.1 | terbium | 0.002 |
| chromium | 1 | neodymium | 0.002 | thallium | 0.05 |
| cobalt | 0.1 | nickel | 1 | thorium | 0.01 |
| copper | 1 | niobium | 0.02 | thulium | 0.002 |
| dysprosium | 0.002 | osmium | 0.005 | tin | 0.05 |
| erbium | 0.002 | palladium | 0.1 | titanium | 5 |
| europium | 0.002 | phosphorus | 100 | tungsten | 0.5 |
| gadolinium | 0.002 | platinum | 0.005 | uranium | 0.01 |
| gallium | 0.1 | potassium | 200 | vanadium | 0.2 |
| germanium | 0.5 | praseodymium | 0.002 | ytterbium | 0.002 |
| gold | 0.05 | rhenium | 0.02 | yttrium | 0.02 |
| hafnium | 0.01 | rhodium | 0.1 | zinc | 1 |
| holmium | 0.002 | rubidium | 0.1 | zirconium | 0.1 |

Example 3—Solubility in Water

The sample was placed in a beaker with 50 ml of water. After thorough agitation, the mixture was centrifuged to separate the dissolved and undissolved portions. The liquid phase was drawn off and placed in a beaker. The solution was evaporated in an oven at 120 degrees C. The dry beaker was then weighed to determine the amount of residue that remained. 19.6% of the original sample had dissolved (or had become finely suspended) as a result of exposure to the water.

Example 4—Solubility Testing in 4% Acetic Acid

The sample was placed in a beaker with 50 ml of 4% acetic acid in water solution. Some effervescence occurred.

After the reaction had run its course, the mixture was centrifuged to separate the dissolved and undissolved portions. The liquid phase was drawn off. The undissolved solid was twice rinsed with water to remove the acetic acid. The solid residue was dried in an oven at 120 degrees C. The dry beaker was then weighed to determine the amount of residue that remained. 11.2% of the original sample remained, indicating that 88.2% of the original sample had dissolved (or had become finely suspended) as a result of exposure to the acetic acid/water solution. Acetic acid does not evaporate to dryness, so it was necessary to calculate the amount of sample that dissolved by difference.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A composition comprising a mineral composition prepared by:
   separating *aloe* leaf rind free from other parts of an *aloe* plant;
   drying the *aloe* leaf rind;
   burning the *aloe* leaf rind to produce an ash; and
   straining the ash burned *aloe* leaf rind.

2. The composition of claim 1, comprising calcium and magnesium obtained from the burning of *aloe* leaf rind in a ratio of about 3:1.

3. The composition of claim 1, wherein the composition is substantially free of lead, cadmium and mercury from the *aloe* leaf rind.

4. The composition of claim 1, wherein the composition comprises less than 200 ppm of aluminum and less than 10 ppm nickel.

5. A formulation comprising a composition according to claim 1 and one or more additional inactive ingredients.

6. The formulation of claim 5, wherein the formulation is a dietary supplement in the form of a powder, tablet or capsule.

7. The formulation of claim 6, further comprising one or more added vitamins, minerals, amino acids, anti-oxidants, other bone building ingredients, or enzymes not from *aloe* rind.

8. The formulation of claim 5, wherein the formulation is a topically administerable composition.

9. The formulation of claim 8, wherein the topical composition is in the form of a lotion, cream, ointment or salve.

10. A method of making a mineral composition comprising the step of:
    obtaining *aloe* leaf rind separated from the *aloe* gel and inner leaf;
    drying the *aloe* leaf rind;
    burning the *aloe* lead rind; and
    straining the burned *aloe* leaf rind to obtain minerals from the *aloe* leaf rind.

11. The composition of claim 1, wherein the *aloe* leaf rind is burned at about 700° C.

12. A composition comprising a mineral composition prepared by a method consisting essentially of the steps of:
    separating *aloe* leaf rind free from other parts of an *aloe* plant;
    drying the *aloe* leaf rind;
    burning the *aloe* leaf rind to produce an ash; and
    straining the ash burned *aloe* leaf rind.

* * * * *